United States Patent
Carrera Fabra et al.

(10) Patent No.: US 12,123,870 B2
(45) Date of Patent: Oct. 22, 2024

(54) FLUIDIC SYSTEM FOR PERFORMING ASSAYS

(71) Applicant: QIAGEN GmbH, Hilden (DE)

(72) Inventors: Jordi Carrera Fabra, Barcelona (ES);
Mathias Kuphal, Barcelona (ES);
Rafael Bru Gibert, Barcelona (ES);
Anna Comengés Casas, Barcelona (ES)

(73) Assignee: QIAGEN GmbH, Hilden (DE)

( * ) Notice: Subject to any disclaimer, the term of this patent is extended or adjusted under 35 U.S.C. 154(b) by 411 days.

(21) Appl. No.: 17/018,199

(22) Filed: Sep. 11, 2020

(65) Prior Publication Data

US 2020/0408752 A1    Dec. 31, 2020

Related U.S. Application Data

(62) Division of application No. 15/210,734, filed on Jul. 14, 2016, now Pat. No. 10,775,370.
(Continued)

(51) Int. Cl.
*B01L 3/00* (2006.01)
*C12Q 1/68* (2018.01)
*G01N 33/543* (2006.01)

(52) U.S. Cl.
CPC ...... *G01N 33/54366* (2013.01); *B01L 3/5027* (2013.01); *C12Q 1/68* (2013.01);
(Continued)

(58) Field of Classification Search
None
See application file for complete search history.

(56) References Cited

U.S. PATENT DOCUMENTS 5,372,948 A * 12/1994 Yip .................. G01N 33/726
435/7.1
5,879,635 A *  3/1999 Nason ................ B01L 3/0272
206/209

(Continued)

FOREIGN PATENT DOCUMENTS

AU          758407 B2    3/2003
AU      2003200701 B2    5/2003
(Continued)

OTHER PUBLICATIONS

Search Report directed to related Japanese Patent Application No. 2018-502221, mailed Jul. 30, 2020, with attached English-language machine translation; 28 pages.
(Continued)

*Primary Examiner* — Robert T. Crow
(74) *Attorney, Agent, or Firm* — Sterne, Kessler, Goldstein & Fox P.L.L.C.

(57) ABSTRACT

A fluidic testing system and method for use are presented. The fluidic testing system includes a microfluidic channel, a first chamber and second chamber. The microfluidic channel has only one port for the introduction and/or extraction of fluid through the microfluidic channel. The first chamber is disposed at a terminal end of the microfluidic channel. The second chamber is coupled to the fluidic channel and is aligned such that each opening to the second chamber is configured to be aligned substantially parallel to a gravity vector during operation.

11 Claims, 7 Drawing Sheets

Related U.S. Application Data

(60) Provisional application No. 62/193,884, filed on Jul. 17, 2015.

(52) U.S. Cl.
CPC .................. *B01L 2200/0605* (2013.01); *B01L 2200/0684* (2013.01); *B01L 2200/16* (2013.01); *B01L 2300/0816* (2013.01); *B01L 2300/0864* (2013.01); *B01L 2300/087* (2013.01); *B01L 2300/0883* (2013.01); *B01L 2400/0457* (2013.01); *B01L 2400/0487* (2013.01)

(56) References Cited

U.S. PATENT DOCUMENTS

| | | | |
|---|---|---|---|
| 5,922,591 A * | 7/1999 | Anderson | B01F 35/71 422/68.1 |
| 6,004,515 A | 12/1999 | Parce et al. | |
| 6,124,138 A | 9/2000 | Woudenberg et al. | |
| 7,678,547 B2 * | 3/2010 | Eyal | F04B 19/006 435/7.1 |
| 7,790,118 B2 | 9/2010 | Maltezos et al. | |
| 8,672,532 B2 | 3/2014 | Jovanovich et al. | |
| 8,697,377 B2 * | 4/2014 | Burd | G01N 35/028 435/7.92 |
| 9,063,121 B2 | 6/2015 | Bru Gibert et al. | |
| 9,132,396 B2 | 9/2015 | Churski et al. | |
| 9,163,279 B2 | 10/2015 | Wakeley et al. | |
| 9,176,126 B2 | 11/2015 | Holmes et al. | |
| 9,855,553 B2 | 1/2018 | Bru Gibert et al. | |
| 10,023,897 B2 | 7/2018 | Mori et al. | |
| 10,775,370 B2 | 9/2020 | Carrera Fabra et al. | |
| 2004/0007275 A1 | 1/2004 | Hui Liu et al. | |
| 2007/0054293 A1 | 3/2007 | Liu et al. | |
| 2007/0297949 A1 | 12/2007 | Wu et al. | |
| 2008/0274905 A1 | 11/2008 | Greene | |
| 2008/0311665 A1 * | 12/2008 | Ryan | G01F 1/7086 436/52 |
| 2009/0148847 A1 | 6/2009 | Kokoris et al. | |
| 2009/0148933 A1 | 6/2009 | Battrell et al. | |
| 2009/0325276 A1 | 12/2009 | Battrell et al. | |
| 2010/0009431 A1 | 1/2010 | Cho et al. | |
| 2010/0317093 A1 | 12/2010 | Turewicz et al. | |
| 2012/0064597 A1 | 3/2012 | Clemmens et al. | |
| 2013/0130262 A1 | 5/2013 | Battrell et al. | |
| 2013/0244241 A1 | 9/2013 | Carrera Fabra et al. | |
| 2013/0302809 A1 | 11/2013 | Bru Gibert et al. | |
| 2014/0045191 A1 | 2/2014 | DeJohn et al. | |
| 2017/0014821 A1 | 1/2017 | Carrera Fabra et al. | |

FOREIGN PATENT DOCUMENTS

| | | |
|---|---|---|
| CN | 101126765 A | 2/2008 |
| CN | 102655938 B | 9/2014 |
| EP | 0889751 B1 | 9/1999 |
| EP | 2436446 A1 | 4/2012 |
| KR | 10-2010-0007720 A | 1/2010 |
| RU | 2011139195 A | 4/2013 |
| WO | WO 2013/172003 A1 | 11/2013 |
| WO | WO 2014/190258 A1 | 11/2014 |

OTHER PUBLICATIONS

Notification of the First Office Action by the China National Intellectual Property Administration, 9 pages, Dec. 31, 2019.
International Search Report and Written Opinion of the International Search Authority directed to related International Patent Application No. PCT/IB2016/054245, Oct. 12, 2016; 11 pages.
International Preliminary Report on Patentability of the International Searching Authority directed to related International Patent Application No. PCT/IB2016/054245, issued Nov. 2, 2017; 9 pages.

* cited by examiner

FLUIDIC SYSTEM FOR PERFORMING ASSAYS

CROSS REFERENCE TO RELATED APPLICATIONS

This application is a divisional of U.S. patent application Ser. No. 15/210,734, filed on Jul. 14, 2016, which claims the benefit of U.S. provisional application No. 62/193,884, filed on Jul. 17, 2015, which are incorporated herein in their entireties by reference.

BACKGROUND

Field

Embodiments of the present invention relate to the field of clinical diagnostic tools.

Background

Given the complexity of the automation of molecular testing and immunoassay techniques, there is a lack of products that provide adequate performances to be clinically usable in near patient testing settings. Typical molecular testing includes various processes involving the correct dosage of reagents, sample introduction, lysis of cells to extract DNA or RNA, purification steps, and amplification for its subsequent detection. Even though there are central laboratory robotic platforms that automate some of these processes, for many tests requiring a short turnaround time, the central laboratory cannot provide the results in the needed time requirements.

However, it is difficult to implement systems in a clinical setting that provide accurate, trustworthy results at a reasonable expense. Given the complicated nature of various molecular testing techniques, the results are prone to error if the testing parameters are not carefully controlled or if the environmental conditions are not ideal.

The fact that molecular techniques have exceptional sensitivity levels at concentrations lower than the previous reference methods makes it rather difficult to obtain clinically relevant conclusions, while avoiding erroneous calls with false positives. To minimize this problem, especially for the detection of pathogen microorganisms, tests should have quantification capability. It has therefore become increasingly necessary to perform multiplexed assays and arrays of tests to consolidate enough data to make confident conclusions. While techniques such as microarray immunoassays provide very high multiplexing capacity, their main limitation is the low speed in obtaining the results, which often have no positive impact on patient management.

SUMMARY

A fluidic testing system and method of use are presented. Simultaneous fluid control of each testing site can reduce testing time and enhance the probability of obtaining repeatable results among the various testing sites.

In an embodiment, a fluidic testing system includes a microfluidic channel, a first chamber and a second chamber. The microfluidic channel has only one port for the introduction and/or extraction of fluid through the microfluidic channel. The first chamber is disposed at a terminal end of the microfluidic channel. The second chamber is coupled to the fluidic channel and is aligned such that each opening to the second chamber is configured to be aligned substantially parallel to a gravity vector during operation.

An example method is described. The method includes flowing a liquid through the only port of a microfluidic channel until the liquid reaches one or more reagents stored in a first chamber coupled to the microfluidic channel. Afterwards, the method includes re-suspending at least a portion of the one or more reagents within the liquid to form a target liquid. The target liquid is then flown through the microfluidic channel and away from the first chamber. The method then includes flowing the target liquid back and forth within the microfluidic channel, such that the target liquid flows through a second chamber coupled to the microfluidic channel. The method includes reacting at least a portion of the one or more re-suspended reagents within the target liquid with one or more reagents disposed within the second chamber and flowing the target liquid out of the microfluidic channel via the only port of the microfluidic channel. The method may include measuring an optical signal from the second chamber, wherein the optical signal is associated with a concentration of the one or more re-suspended reagents within the second chamber.

In another embodiment, a fluidic testing system includes a microfluidic channel, a plurality of chambers, and a chamber disposed at a terminal end of the microfluidic channel. The microfluidic channel has only one port for the introduction and/or extraction of fluid through the microfluidic channel. Each of the plurality of chambers is coupled to the microfluidic channel in a series arrangement, such that a length of each of the plurality of chambers is aligned substantially parallel to a gravity vector.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 1A is a graphical representation of a test cartridge system, according to an embodiment.

FIG. 1B displays another view of the test cartridge system, according to an embodiment.

Figure 1A:
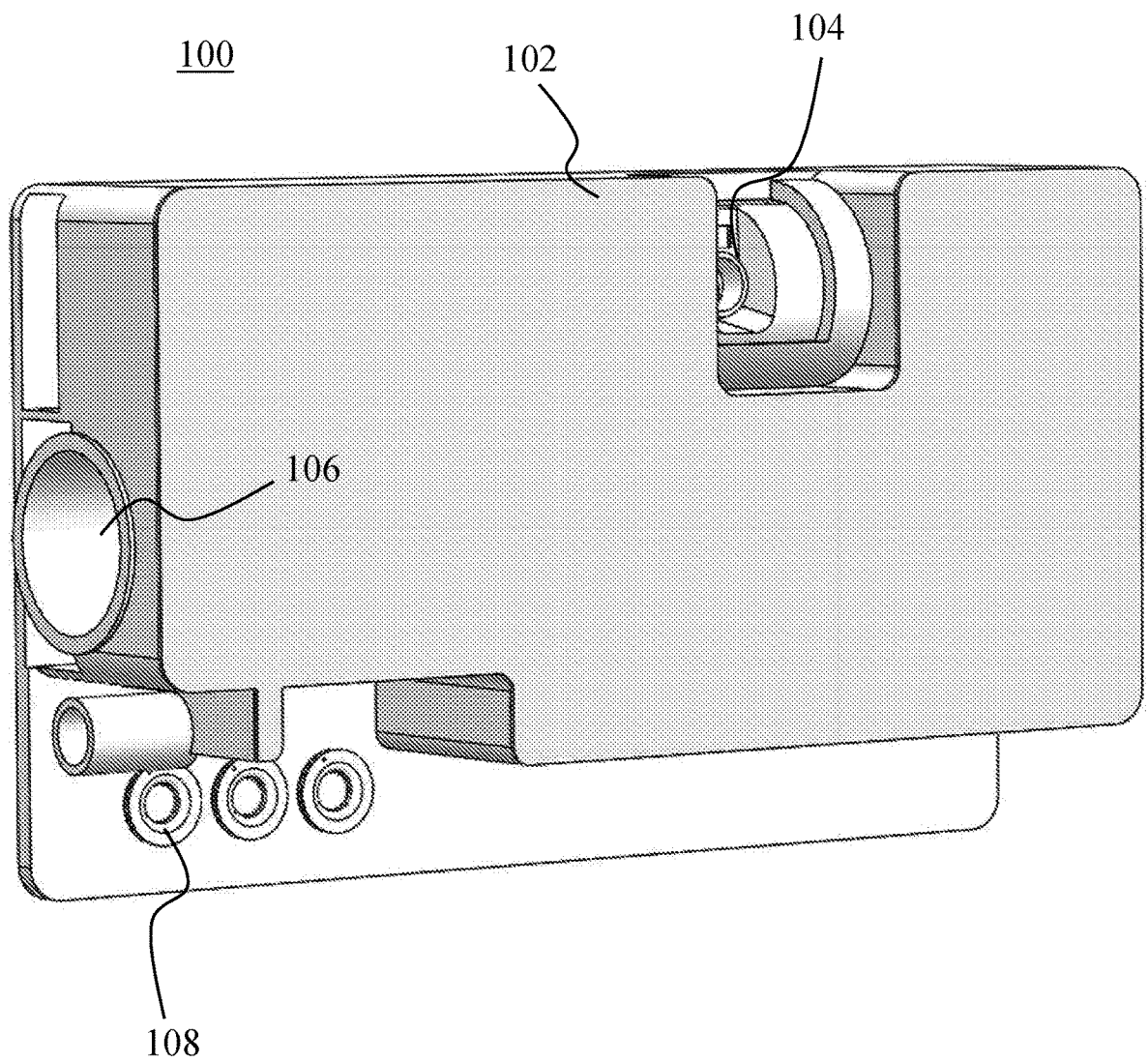

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Some embodiments described herein relate to a microfluidic arrangement integrated within a test cartridge system for performing a variety of molecular tests, such as immunoassays, PCR, DNA hybridization, etc. In an embodiment, the test cartridge integrates all of the components necessary to perform such tests into a single, disposable package. The test cartridge may be configured to be analyzed by an external measurement system which provides data related to the reactions that take place within the test cartridge. In an embodiment, the test cartridge includes a plurality of testing chambers with a transparent window to perform optical detection with each testing chamber.

In one example, a single test cartridge may be used to perform an array of immunoassays with a given sample. The test cartridge contains all of the necessary buffers, reagents, and labels held in sealed chambers integrated into the cartridge to perform the immunoassays.

One of the main limitations of molecular diagnostic instrumentation is the problem associated with contamination such as cross-contamination, carry-over contamination, etc. Embodiments described herein substantially eliminate by design the contamination of samples to the instrument.

In one embodiment, the test cartridge offers a self-contained liquid or dried reagents sealed during the manufacturing process. The reagents and the introduced sample do not enter into contact with the environment or with any part of the instrument. This feature of the test cartridge is also important for many laboratories and hospitals to safely dispose of the products after their use.

In order to perform an array of tests, the test cartridge contains a plurality of testing chambers as well as a plurality of fluidic channels. The fluidic channels may be designed to connect the various testing chambers together, and transfer liquid to other portions of the test cartridge. The fluidic channels may be designed to facilitate performing immunoassays within connected chambers along the fluidic channels.

Some details relating to the components of the test cartridge system are described herein with references made to the figures. It should be understood that the illustrations of each physical component are not meant to be limiting and that a person having skill in the relevant art(s) given the description herein would recognize ways to re-arrange or otherwise alter any of the components without deviating from the scope or spirit of the invention. A more detailed explanation of the test cartridge system may be found in co-pending U.S. application Ser. No. 13/836,845, the disclosure of which is incorporated by reference herein in its entirety.

FIG. 1A illustrates an example test cartridge system 100, according to an embodiment. Test cartridge system 100 includes a cartridge housing 102, which may house a variety of fluidic chambers, channels, and reservoirs. Samples may be introduced into cartridge housing 102 via sample port 104, according to an embodiment. In an example, sample port 104 receives solid, semi-solid, or liquid samples. Sample port 104 may also be designed to receive a needle of a syringe in order to inject a sample into a chamber or fluidic channel within cartridge housing 102. In another embodiment, cartridge housing 102 includes more than one inlet to introduce samples. Further details about the various chambers and channels of cartridge system 100 may be found in co-pending U.S. application Ser. No. 13/836,845.

According to an embodiment, cartridge system 100 may include a transfer chamber that moves laterally along a guide 106 within cartridge housing 102. This transfer chamber may be used to align various fluid ports with the transfer chamber and control movement of the fluid throughout the various fluidic channels and chambers of cartridge system 100.

Cartridge system 100 includes one or more through-holes 108 according to an embodiment. Through-holes 108 may be located on a thinner portion of cartridge system 100. In one example, this thinner portion is located away from many of the fluid chambers within cartridge housing 102. Through-holes 108 allow for various reagents to be placed within through-holes 108, effectively "plugging" the holes. As such, the reagents may be disposed upon small plugs that fit snugly within through-holes 108. Examples of reagents may include immobilized antibodies, proteins, enzymes, and single-stranded or double-stranded DNA or RNA. A gasket seal may be used around the edges of the plug to ensure a substantially leak-proof fit. Further details of these plugs are described below with reference to FIG. 4.

Figure 1B:
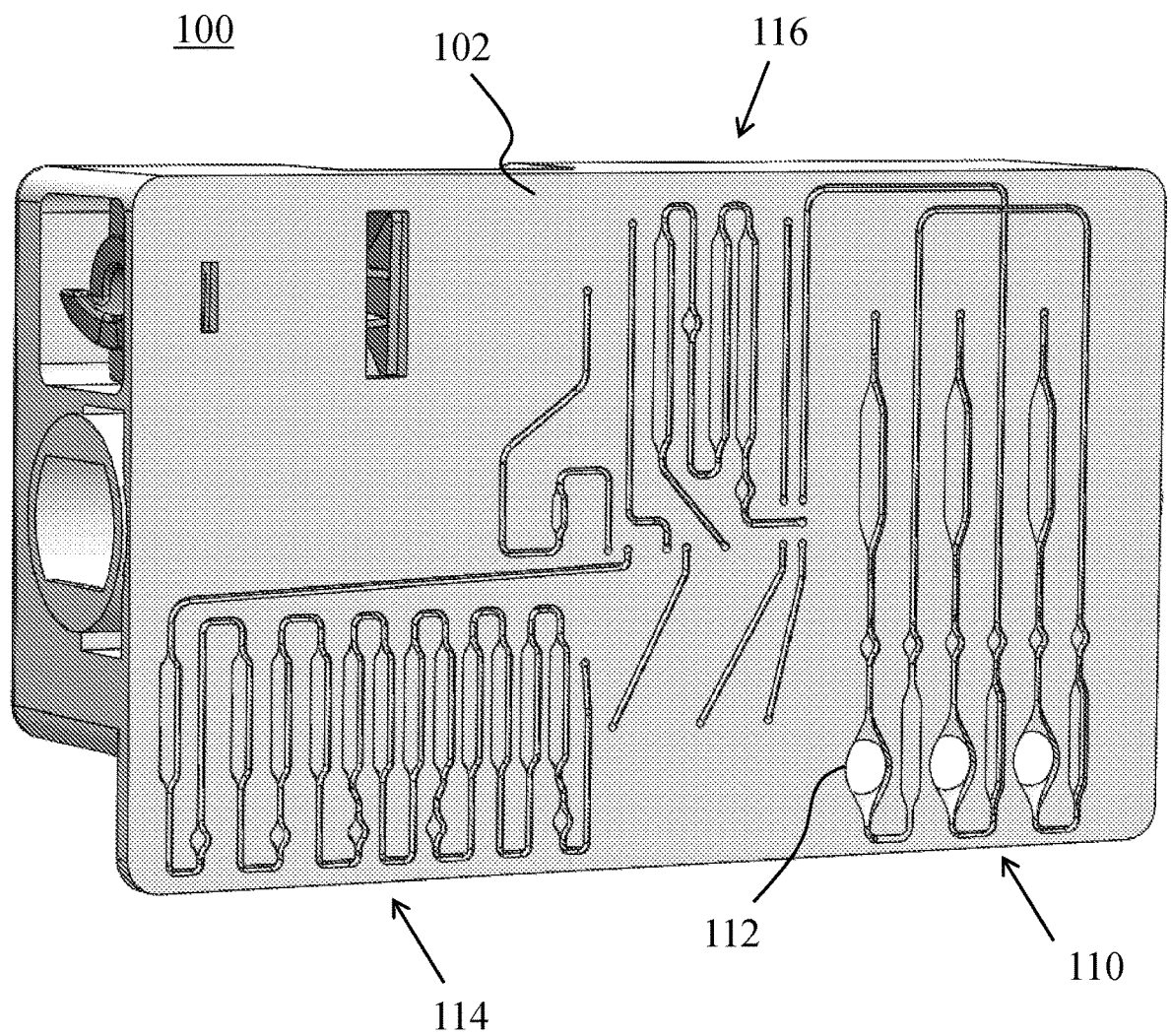

FIG. 1B illustrates a view of a backside of the example test cartridge system 100, according to an embodiment. Numerous fluidic channels can be seen within cartridge housing 102. In one example, these fluidic channels are microfluidic channels, where the fluid flow through the channels is in the laminar flow regime. As such, the dimensions of the microfluidic channels may have cross sections less than, for example, 5 mm$^2$, less than 1 mm$^2$, less than 10,000 µm$^2$, less than 5,000 µm$^2$, less than 1,000 µm$^2$, or less than 500 µm$^2$.

According to an embodiment, various fluidic testing areas are incorporated within cartridge housing 102. For example, a testing area 110 may include a plurality of fluidic testing arrangements, each having an opening 112 that is aligned with one of the through-holes 108 from the other side of test cartridge 100. As such, each of openings 112, when plugged with reagents, defines a testing chamber for various biological and chemical tests. These tests may involve immunoassays, enzyme interactions, cellular responses, or DNA hybridization, just to name a few. Other tests to be performed would be apparent to one of ordinary skill in the art given the disclosure herein. Further details regarding each of the testing arrangements illustrated in testing area 110 are described below with reference to FIG. 2.

Another fluidic area 114 includes a plurality of chambers connected in a series arrangement, according to an embodiment. These chambers may be used for dilutions and to provide accurate dosing concentrations to other chambers and fluidic channels within the system. Further details regarding the illustrated fluidic area 114 are described below with reference to FIG. 5. Other various fluidic channels 116 are shown as well and may be used to guide fluid between various chambers within cartridge housing 102, and fluid to/from the various chambers to any of the channels shown in testing area 110 or fluidic area 114.

Figure 2:
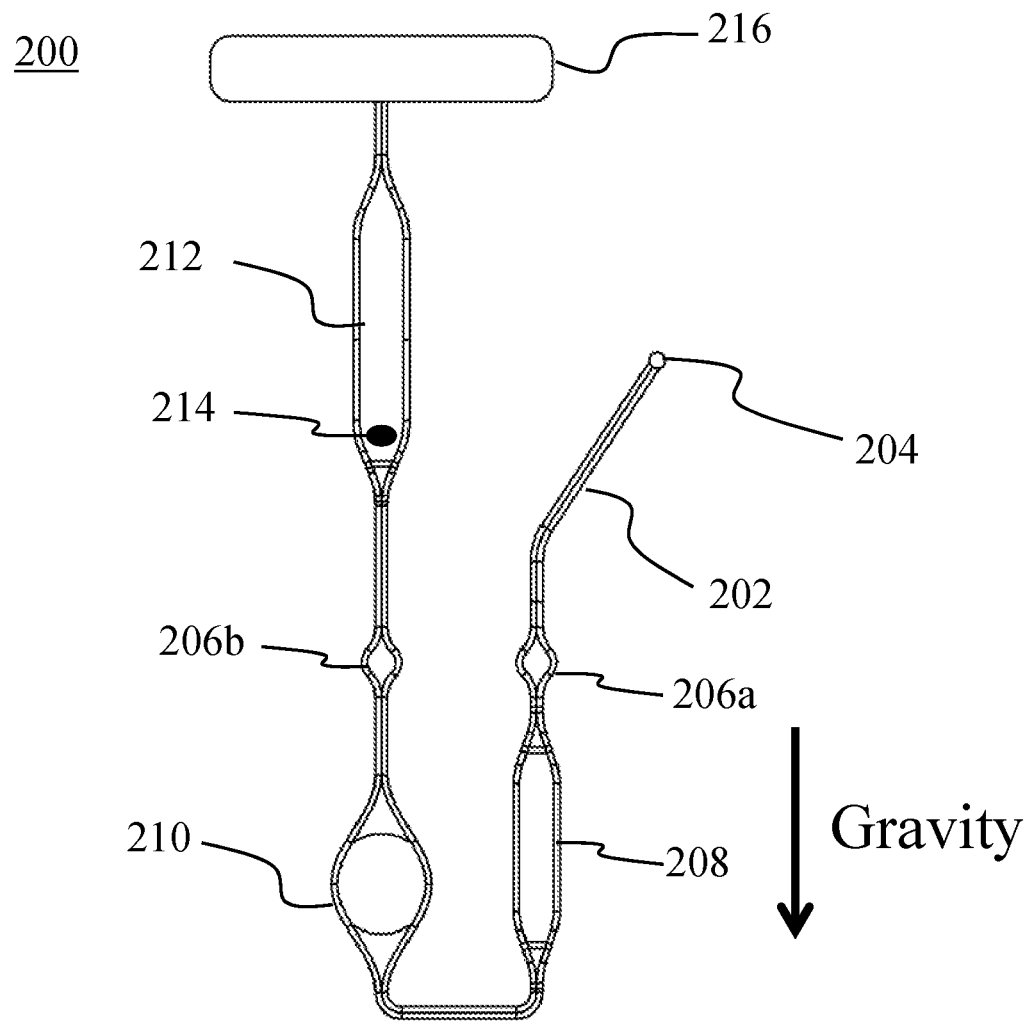
FIG. 2 illustrates a fluidic testing arrangement, according to an embodiment.

FIG. 2 illustrates an example of a fluidic testing arrangement 200, according to an embodiment. A gravity vector is also shown to provide the orientation that fluidic testing arrangement 200 is designed to be used for maximum effectiveness, according to one example. Other orientations may be possible as well, although the other orientations may cause unwanted air bubbles to form within the channels.

Fluidic testing arrangement 200 includes a microfluidic channel 202 having only one port 204, according to an embodiment. The other end of microfluidic channel 202 terminates at a closed chamber 216. This closed chamber acts as a reservoir for the air that is trapped within microfluidic channel 202 as fluid is pushed through microfluidic channel 202 via port 204. The inclusion of closed chamber 216 replaces the need for using a vent to allow the air to escape the system. Not having a vent provides advantages such as reducing the probability of leakage and contamination.

Microfluidic channel 202 may have one or more chambers or enlarged areas disposed along a length of microfluidic channel 202. For example, microfluidic channel 202 may include one or more channel enlargements 206, such as 206a and 206b. Channel enlargements 206a and 206b may act as liquid sensing areas. As such, channel enlargements 206a and 206b may be used along with one or more external optical probes to determine whether or not liquid is present within channel enlargements 206a and 206b. This determination may be used to activate other functions of test cartridge system 100. In another embodiment, channel enlargements 206a and 206b may include integrated sensors, such as a patterned resistive sensor, to indicate the presence or flow rate of the fluid.

Microfluidic channel 202 may also be coupled with a mixing chamber 208. In an embodiment, mixing chamber 208 has a larger cross-sectional dimension than the microfluidic channel 202. This larger cross sectional dimension may be chosen such that the fluid regime within mixing chamber 208 is no longer laminar, but turbulent. By varying the pressure applied to port 204, a sample solution may be moved back and forth within mixing chamber 208, thus providing a passive mixing of the fluid. According to an embodiment, mixing chamber 208 is aligned such that the openings to mixing chamber 208 are substantially aligned with the gravity vector. This alignment helps to reduce the creation of air bubbles within the chamber as the fluid is being mixed.

Microfluidic channel 202 also includes a testing chamber 210. In one example, testing chamber 210 is located further downstream than mixing chamber 208 within microfluidic channel 202. Testing chamber 210 may be aligned over one of the through-holes 108 illustrated in FIG. 1A. As such, reagents may be placed into testing chamber 210 by "plugging" one side of testing chamber 210, using a plug insert as illustrated in FIG. 4. The geometry of testing chamber 210 allows for a large surface area for interaction with various reagents in testing chamber 210. For example, the diameter of testing chamber 210 may be chosen to be substantially similar to that of a single plate of a standard-sized 96-well plate, 24-well plate, 48-well plate, or 384-well plate. The fluid volume within testing chamber 210 may be less than 50 µL. In one example, the fluid volume within testing chamber 210 is between 10 and 30 µL. The volume of testing chamber 210 may be designed large enough to be completely filled by a 50 µL sample solution. In an embodiment, the openings of testing chamber 210 are aligned substantially parallel to the gravity vector. With the openings aligned in this way, the chamber may be placed along fluidic channel such that fluid can fill the chamber from the bottom-up. By filling testing chamber 210 in this way, the generation of air bubbles may be reduced. In one embodiment, testing chamber 210 may include a plurality of beads to increase the surface area for reagent interaction. By varying the pressure applied to port 204, the sample solution may be moved back and forth within testing chamber 210, to maximize the interaction between the reagents immobilized within testing chamber 210 and the reagents within the sample solution.

The larger cross sectional dimension of testing chamber 210 may be chosen such that the fluid regime within testing chamber 210 is no longer laminar, but turbulent. This turbulent flow increases the reaction kinetics between immobilized reagents in testing chamber 210 and reagents within the solution. According to an embodiment, testing chamber 210 is aligned such that the openings to testing chamber 210 are substantially aligned with the gravity vector. This alignment helps to reduce the creation of air bubbles within the chamber as the sample solution is moved back and forth in testing chamber 210.

Detection of reagent interactions within testing chamber 210 may occur using an external optical source and photodetector coupled to an analyzer in which test cartridge system 100 is placed. Thus, any walls or covers of testing chamber 210 may be transparent to allow for optical detection. In one example, the photodetector measures absorbance through the liquid within testing chamber 210 at one or more wavelengths. In another example, the photodetector measures a fluorescence signal generated from a fluorescent compound within testing chamber 210. In an embodiment, the fluorescence measurements are taken from beneath testing chamber 210. Testing chamber 210 may be adapted for other means of detection, e.g., electrochemical, electromechanical, surface plasmon resonance, time-resolved fluorescence, etc.

A storage chamber 212 may be located along microfluidic channel 202 and further downstream of testing chamber 210. Storage chamber 212 may include dry chemicals, such as frozen or lyophilized analytes. In another example, storage chamber 212 includes dry reagents 214 or biological samples. The biological samples may be freeze dried within storage chamber 212. Such biological or chemical compounds may be stored in storage chamber 212 for long periods of time before use. The dimensions of storage chamber 212 may be designed to specifically fit the size of dried reagents 214 (such as a dried chemistry bead), usually on the order of a few millimeters in diameter, according to one embodiment. In one example, fluid drawn towards storage chamber 212 mixes with and re-suspends the dried reagents 214 within the fluid. The liquid having the resuspended reagents may then be drawn back towards testing chamber 210 for analysis.

The various chambers along microfluidic channel 202 may be strategically placed depending on the application and test being performed. For example, in the arrangement illustrated in FIG. 2, a buffer liquid may be forced, via an applied positive pressure, through port 204 and all the way around to storage chamber 212 to re-suspend the dried reagents 214 within the buffer solution to form a test solution. Next, the test solution may be drawn back through microfluidic channel 202, via a negative pressure applied at port 204, or by releasing the positive pressure applied previously. The test solution may be brought back all the way to channel enlargement 206a. After this, the fluid may be forced back and forth between channel enlargement 206a and storage chamber 212 multiple times, passing through both mixing chamber 208 and testing chamber 210. In this way, the fluid continues to be mixed via mixing chamber 208 while interacting with the captured reagents within testing chamber 210. In the example of an immunoassay, capture antibodies are immobilized within testing chamber 210 while proteins present within the test solution are introduced to the capture antibodies. A binding reaction may indicate a positive test result (and produce a florescent signal). Once the test solution has been introduced enough times through testing chamber 210, it may be drawn out of port 204, and a different wash solution may be introduced to wash away any unbound material within testing chamber 210 (e.g., in an effort to eliminate false positives). The wash solution can be introduced over the analytes within testing chamber 210 without having to pass through storage chamber 212. This is advantageous as it avoids possible re-suspension of any of the dry chemicals left in storage chamber 212. It should be understood that this is just one example use of fluidic testing arrangement 200, and that the arrangement of chambers may be changed based on the application.

Figure 3:
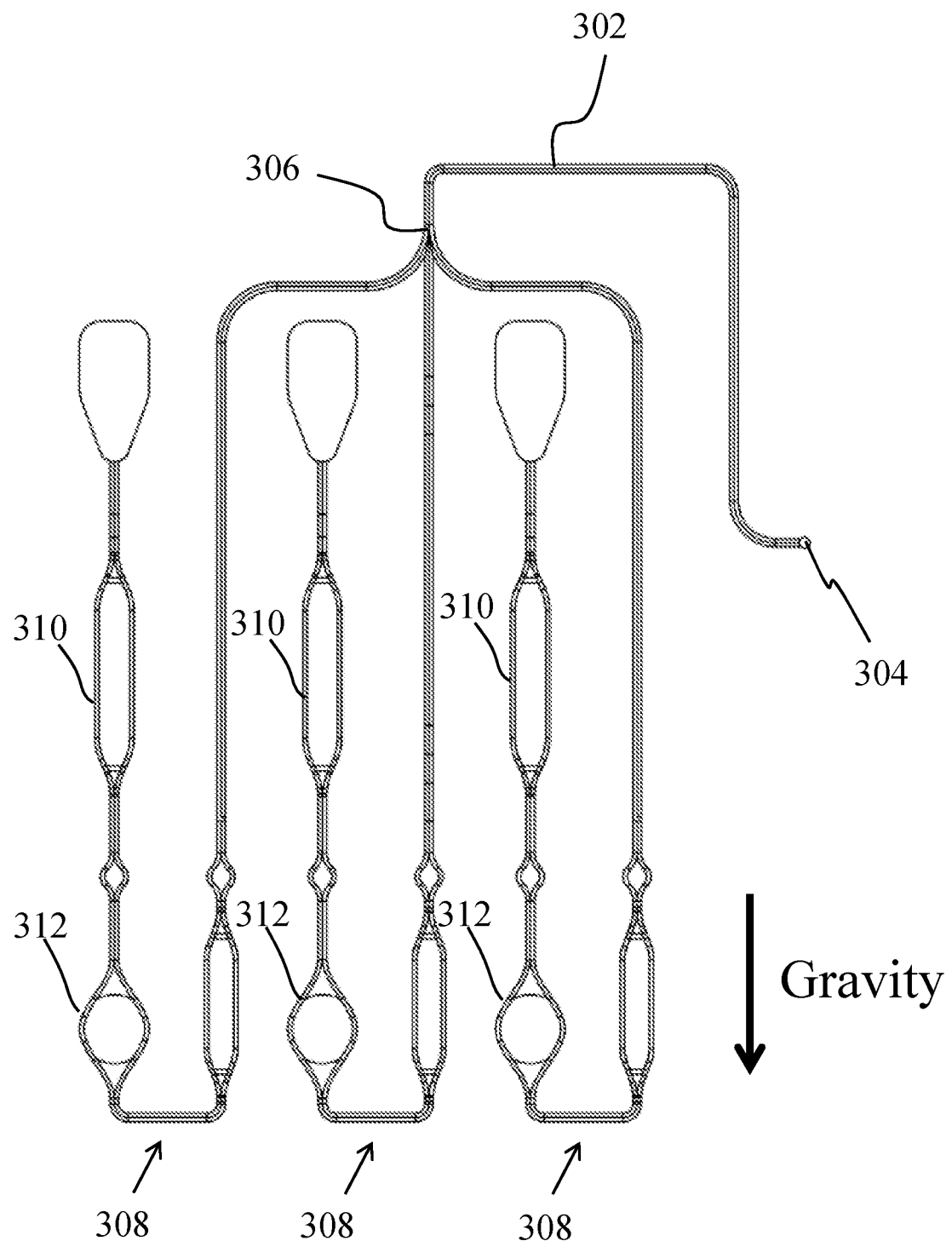
FIG. 3 illustrates a plurality of fluidic testing arrangements, according to an embodiment.

FIG. 3 illustrates a plurality of fluidic testing arrangements connected to the same input fluidic channel 302, according to an embodiment. Input fluidic channel 302 includes a single port 304 for the introduction and expulsion of liquid, and for applying, or releasing, pressure to the liquid. Input fluidic channel 302 may be coupled to a fluidic junction 306 where a single fluidic channel splits into a plurality of fluidic channels. In one example, each of the plurality of fluidic channels feeds its own testing arrangement 308. Although only three testing arrangements 308 are illustrated as connected to input fluidic channel 302, it should be understood that any number and type of fluidic testing arrangements may be coupled to input fluidic channel 302.

Storage chamber 310 within each testing arrangement 308 may include a different concentration of reagents or different reagents altogether from other storage chambers 310. Similarly, the reagents placed within testing chamber 312 within each testing arrangement 308 may include a different concentration of reagents or different reagents altogether from other testing chambers 312. In this way, a multiplexed array of experiments may be performed from the same input fluidic channel 302.

Figure 4A:
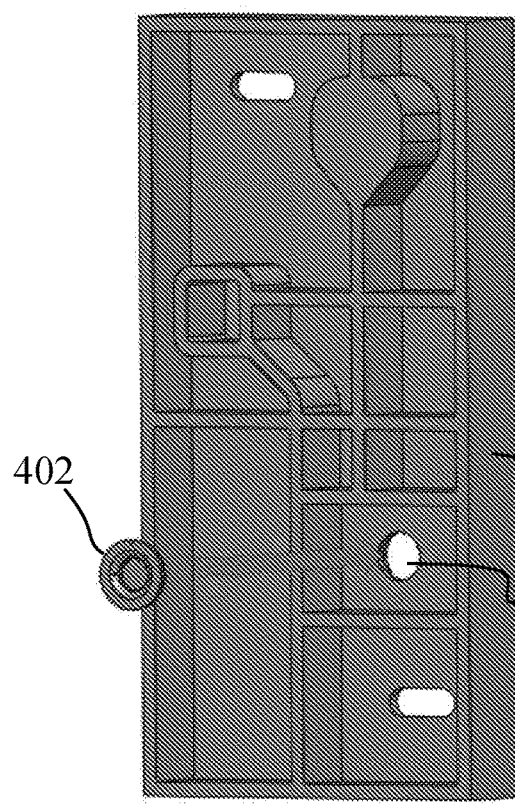
FIGS. 4A-4B illustrate views of a fluidic testing arrangement, according to some embodiments.
Figure 4B:
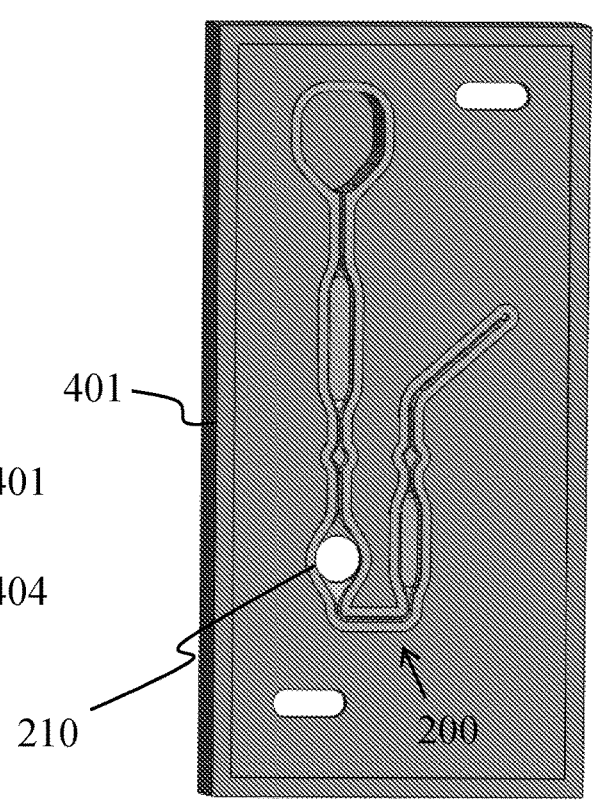

FIGS. 4A and 4B illustrate a procedure for placing a reagent insert 402 within a testing chamber 210 that is part of a fluidic testing arrangement 200, according to an embodiment. It should be understood that the illustrations in FIGS. 4A and 4B are not intended to be limiting to the design of the fluidic system in any way, and are merely provided to demonstrate how reagent insert 402 can be used.

Reagent insert 402 may be shaped to snugly fit within a hole 404 on the backside of housing 401, while hole 404 is aligned within testing chamber 210 on the front side of housing 401. Reagent insert may include a gasket seal around its edge to help prevent any fluid leaks after it has been placed within hole 404. One side of reagent insert 402 may include a variety of reagents to be used within testing chamber 210. For example, reagent insert 402 may include a surface having specific capture antibodies to be used in an immunoassay. The reagents may be freeze dried upon a surface of reagent insert 402, or may be coated on top of insert 402. Insert 402 may include a protective coating that dissolves when in contact with fluid. According to one embodiment, reagent insert 402 may be removed from hole 404 at any time to be replaced with a different reagent insert. Reagent insert 402 may be secured to the cartridge by means of any retention structure or adhesive as would be understood by a person skilled in the art.

Figure 5:
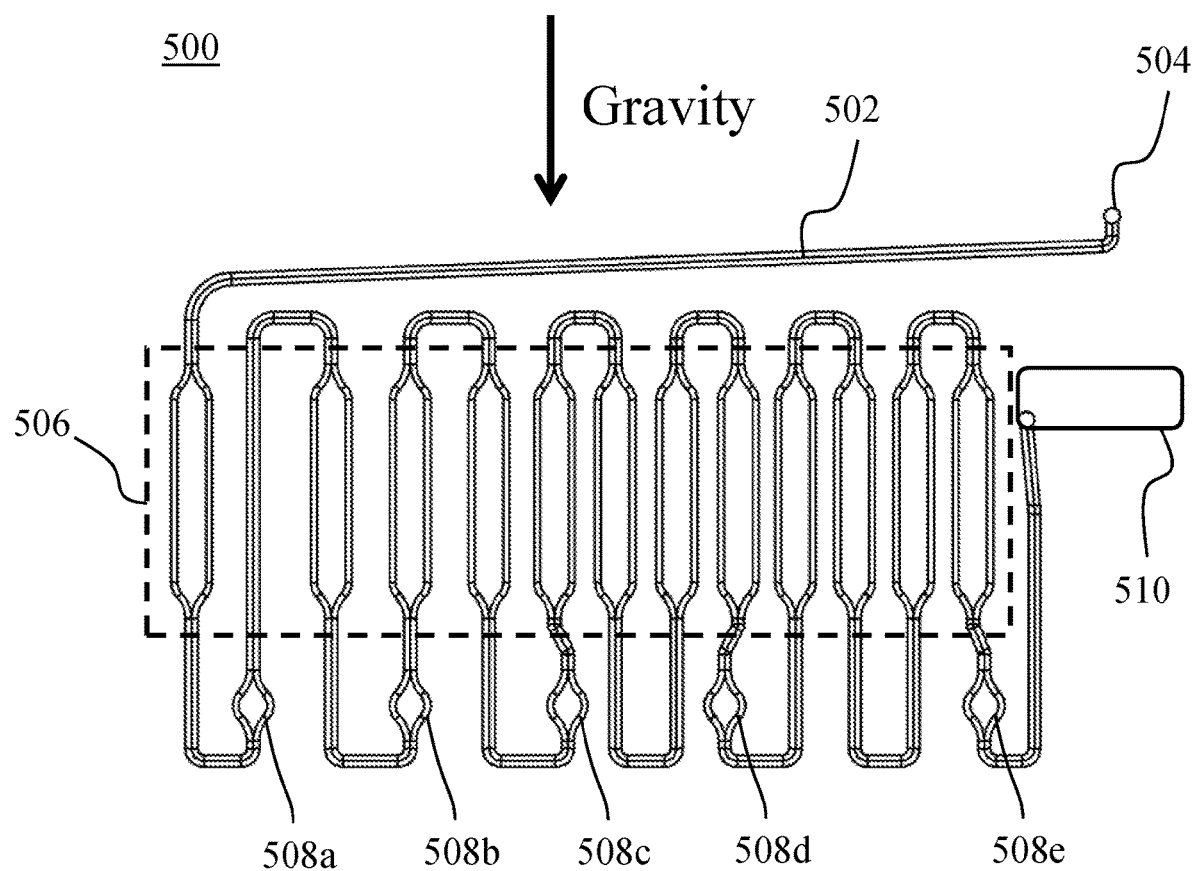
FIG. 5 illustrates another fluidic testing arrangement, according to an embodiment.

FIG. 5 illustrates another fluidic arrangement 500, according to an embodiment. A microfluidic channel 502 includes only one port 504 and couples between chambers 506, which are arranged in series along microfluidic channel 502. In one example, microfluidic channel 502 follows a serpentine path with chambers 506 aligned horizontally along that path as illustrated in FIG. 5. Each individual chamber may be defined as having a length longer than its width, with the length aligned substantially parallel with a gravity vector as shown. Additionally, the openings at the top and bottom of each of chambers 506 are aligned with the gravity vector. According to an embodiment, microfluidic channel 502 terminates at an enclosed chamber 510. Enclosed chamber 510 may be designed as a reservoir for the air that is forced through microfluidic channel 502 as liquid enters through port 504. Each chamber of the plurality of chambers may have a fluid volume of less than 250 µl, less than 100 µl, or less than 50 µl.

Microfluidic channel 502 may also include a plurality of channel enlargements 508a-508e. Channel enlargements 508a-508e may act in a similar way as previously discussed with reference to FIGS. 2 and 3. Channel enlargements 508a-508e may be arranged along microfluidic channel 502 such that the number of chambers 506 between adjacent channel enlargements is variable. In this context, adjacent channel enlargements describes any two channel enlargements that do not have another channel enlargement between them along the path of microfluidic channel 502. In other words, an example pattern of channel enlargements 508 (CE) and chambers 506 (CH) as fluid moves down microfluidic channel 502 towards enclosed chamber 510 is: CE; CH; CE; CH; CH; CE; CH; CH; CH; CH; CE; CH; CH; CH; CH; CE.

According to an embodiment, fluidic arrangement 500 may be used for performing dilutions, reagent dosings, or various mixing steps. Chambers 506 may also be used to store various fluids for later use. For example, reagent solutions of different concentrations can be stored within chambers 506 with a lowest concentration at the far left chamber and with increasing concentrations for each chamber to the right until the highest concentration in the far right chamber of chamber 506. Alternatively, a highest concentration may be in the far left chamber of chambers 506, with decreasing concentrations for each chamber to the right until the lowest concentration in the far right chamber of chamber 506.

In one example, a first liquid enters through port 504 up until it reaches channel enlargement 508a. A liquid sensor is used at channel enlargement 508a to determine the presence of the first liquid. When the first liquid is determined to be at channel enlargement 508a, a signal may be sent to stop flowing in the first liquid. Afterwards, a second liquid is flown through port 504 until it reaches a different channel enlargement further downstream (any one of 508b-508e.) This may be repeated with other liquids following the second liquid. In this way, known concentrations of two or more liquids may be stored within chambers 506.

Figure 6:
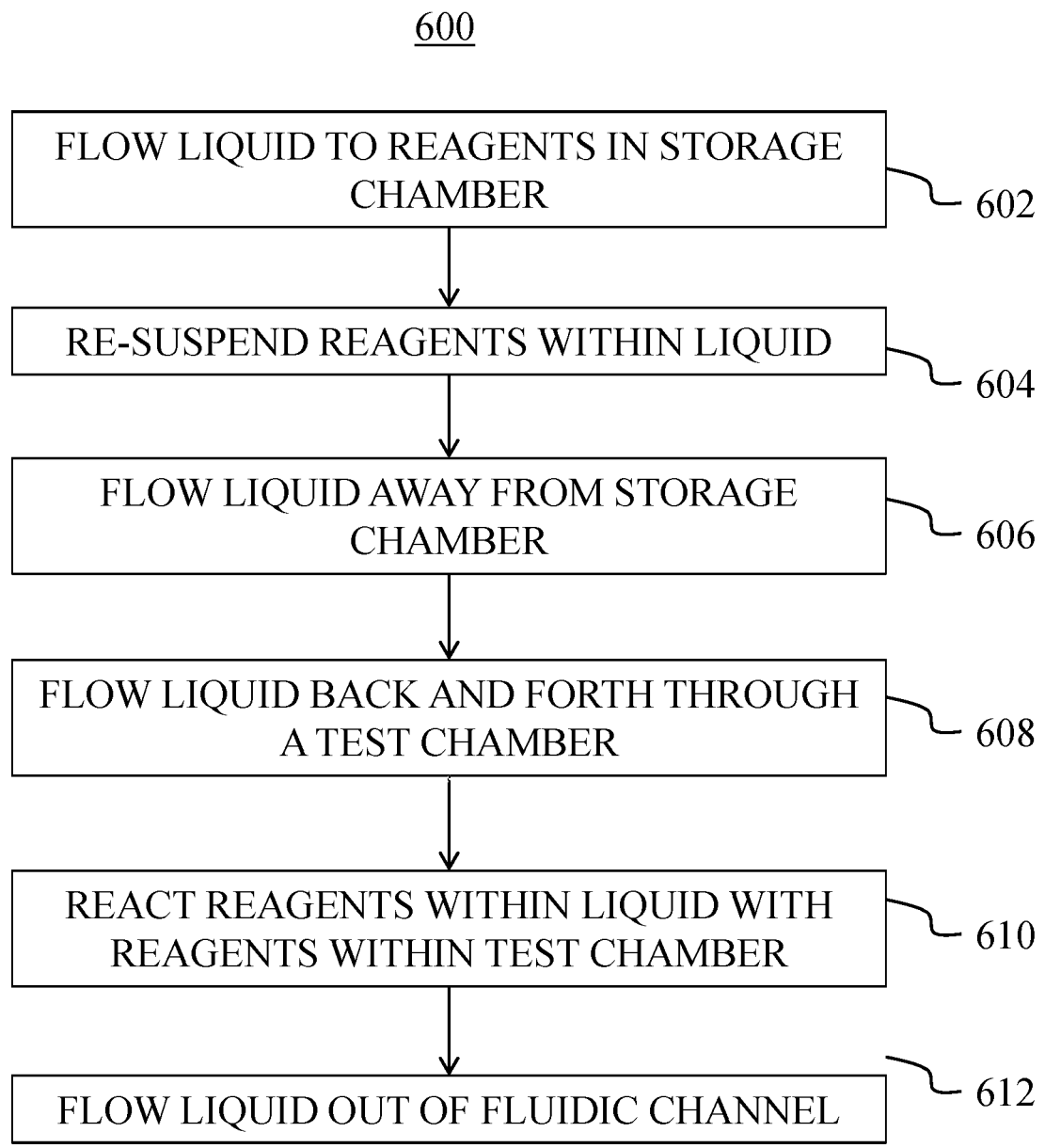
FIG. 6 illustrates an example fluidic testing method, according to an embodiment.

FIG. 6 is a flow chart illustrating a method 600 for using a fluidic testing arrangement, according to an embodiment. It should be understood that the steps shown in method 600 are not exhaustive and that other steps may be performed as well without deviating from the scope or spirit of the invention.

At block 602, liquid is flown through a fluidic channel (e.g., via an applied pressure) until it reaches reagents stored in a storage chamber, according to an embodiment. The liquid may enter the fluidic channel through a single port, which is the only input/output port of the fluidic channel. The reagents may be, for example, any dried reagents, freeze dried reagents, or reagents contained within a pellet to be dissolved by the liquid. This step may describe liquid moving through microfluidic channel 202 until it reaches dried reagents 214 in storage chamber 212, as illustrated in FIG. 2.

At block 604, the reagents are re-suspended within the liquid. In one example, the liquid may be a buffer solution having properties that allow for the reagents to be dissolved within the buffer and remain stable within the buffer. Once the reagents have been mostly dissolved, the liquid may be referred to as a target liquid for the remaining steps of the process.

At block 606, the target liquid is flown away from the storage chamber. In the example illustrated in FIG. 2, the target liquid would be drawn back through the microfluidic channel and away from storage chamber 212.

At block 608, the target liquid is flown back and forth within the fluidic channel, such that it crosses through a testing chamber, according to an embodiment. This testing chamber may include another set of reagents that react with the re-suspended reagents in the target liquid. The target liquid may be moved back and forth solely within the testing chamber, or through other portions of the fluidic system as well. For example, and with reference to FIG. 2, the target liquid may be moved back and forth between channel enlargements 206a and 206b, such that the target liquid traverses both testing chamber 210 and mixing chamber 208. Passing the liquid multiple times through mixing chamber 208 may be an optional step to provide better mixing of the re-suspended reagents within the target liquid. The liquid may also be moved back and forth between channel enlargement 206a and storage chamber 212.

At block 610, the reagents within the target liquid react with the reagents within the second chamber. This process occurs simultaneously with the movement of the liquid described above in block 608. In the case of an immunoassay, capture antibodies or an antigen sample may be immobilized in the second chamber while target antibodies/antigens bind to the capture antibodies/antigens. Other reactions may include enzymatic reactions that result in a color (e.g., absorbance) change or reactions involving bioluminescent proteins.

At block 612, the target liquid is flown out of the fluidic channel by the single port, according to an embodiment. The target liquid may be removed via applying a negative pressure at the single port, thus drawing the target liquid out. Following the removal of the target liquid, other liquids may be introduced through the fluidic system. For example, various wash liquids may be introduced and flown through the second chamber to wash away any unbound material.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

What is claimed is:

1. A method comprising:
   flowing a liquid through an only fluid port of a fluidic channel in a first direction until the liquid reaches a first set of one or more reagents stored in a first chamber coupled to the fluidic channel, wherein the liquid flows through a second chamber coupled to the fluidic channel before reaching the first chamber;
   re-suspending at least a portion of the first set of one or more reagents within the liquid to form a target liquid;
   flowing the target liquid back through the fluidic channel to the second chamber in a second direction and away from the first chamber;
   flowing the target liquid back and forth within the fluidic channel, such that the target liquid flows through the second chamber;
   reacting at least a portion of the re-suspended first set of one or more reagents within the target liquid with a second set of one or more reagents disposed within the second chamber, the second set of one or more reagents being immobilized on a surface of a reagent insert plugged into a through-hole aligned with the second chamber, wherein the reacting begins once the re-suspended first set of one or more reagents contacts the second set of one or more reagents; and
   flowing the target liquid out of the fluidic channel via the only fluid port of the fluidic channel.

2. The method of claim 1, wherein each opening to the second chamber is aligned substantially parallel to a gravity vector.

3. The method of claim 1, wherein flowing the target liquid back and forth within the fluidic channel comprises flowing the target liquid back and forth between two locations of the fluidic channel.

4. The method of claim 1, further comprising:
   sensing a presence of the liquid at each of the two locations of the fluidic channel.

5. The method of claim 1, wherein flowing the target liquid back and forth within the fluidic channel comprises flowing the target liquid through a third chamber and mixing the target liquid as it flows through the third chamber.

6. The method of claim 1, further comprising:
   measuring an optical signal from the second chamber, wherein the optical signal is associated with a concentration of the re-suspended first set of one or more reagents within the second chamber.

7. The method of claim 1, further comprising:
   flowing a second liquid through the only fluid port of the fluidic channel;

flowing the second liquid back and forth within the fluidic channel, such that the second liquid flows through the second chamber;

flowing the second liquid out of the fluidic channel via the only fluid port of the fluidic channel.

8. The method of claim 7, wherein the second liquid is a wash buffer.

9. The method of claim 1, wherein the reacting comprises binding at least a portion of the re-suspended first set of one or more reagents within the target liquid with the second set of one or more reagents.

10. The method of claim 1, wherein:

the second chamber is aligned with a through-hole of a housing of the fluidic channel; and the method further comprises inserting the second set of one or more reagents into the second chamber via the through-hole.

11. The method of claim 10, wherein the inserting comprises inserting a reagent insert into the through-hole such that the insert fits within the through-hole, wherein the reagent insert has the second set of one or more reagents on a side of the reagent insert.

* * * * *